US012774480B2

(12) United States Patent
Wang et al.

(10) Patent No.: US 12,774,480 B2
(45) Date of Patent: Oct. 27, 2026

(54) METHOD FOR SYNTHESIZING DIGLYCERIDE

(71) Applicants: South China University of Technology, Guangzhou (CN); Guangdong Yue-S Special Nutrition Technology Co., Ltd., Foshan (CN)

(72) Inventors: Yonghua Wang, Guangzhou (CN); Xuan Liu, Guangzhou (CN); Bo Yang, Guangzhou (CN); Weifei Wang, Guangzhou (CN); Dongming Lan, Guangzhou (CN); Riming Luo, Foshan (CN)

(73) Assignees: South China University of Technology, Guangzhou City (CN); Guangdong Yue-S Special Nutrition Technology Co., Ltd., Foshan City (CN)

( * ) Notice: Subject to any disclaimer, the term of this patent is extended or adjusted under 35 U.S.C. 154(b) by 873 days.

(21) Appl. No.: 17/639,703

(22) PCT Filed: Apr. 21, 2020

(86) PCT No.: PCT/CN2020/085883
§ 371 (c)(1),
(2) Date: Mar. 2, 2022

(87) PCT Pub. No.: WO2021/088319
PCT Pub. Date: May 14, 2021

(65) Prior Publication Data
US 2022/0282290 A1 Sep. 8, 2022

(30) Foreign Application Priority Data
Nov. 6, 2019 (CN) ........................ 201911074797.9

(51) Int. Cl.
*C12P 7/6454* (2022.01)

(52) U.S. Cl.
CPC ..... *C12P 7/6454* (2013.01); *C12Y 301/01034* (2013.01)

(58) Field of Classification Search
CPC ........... C12P 7/6454; C12Y 301/01034; C12R 2001/10; C12N 9/20
See application file for complete search history.

(56) References Cited

FOREIGN PATENT DOCUMENTS

| | | | | |
|---|---|---|---|---|
| CN | 1615365 A | * | 5/2005 | ................ C12P 7/62 |
| CN | 1884564 A | | 12/2006 | |

(Continued)

OTHER PUBLICATIONS

Zheng Pingyu, Production of Diacylglycerol with High Purity by Holoenzymatic Process, May 15, 2014.

(Continued)

*Primary Examiner* — Robert J Yamasaki
*Assistant Examiner* — Charles Zoltan Constantine
(74) *Attorney, Agent, or Firm* — The Dobrusin Law Firm, P.C.

(57) ABSTRACT

Disclosed is a method for synthesizing a diglyceride. The diglyceride is obtained by mixing a fatty acid donor with glycerol, partial glyceride lipase, and monoglyceride lipase by adding water, then subjecting the same to an esterification reaction, with a reaction time of 8 to 24 hours, and further separating and purifying the same. In the present invention, monoglyceride lipase is used to promote the reaction efficiency of partial glyceride lipase in the esterification reaction, so as to increase the synthesis rate of diglyceride. Compared with a single enzyme, the synthesis time is shortened by half or more, and 45.50% or more of diglyceride is obtained after the esterification reaction. Since substantially no triglyceride is generated in products, the content of DAG reaches 98% or more after the same has been purified by means of molecular distillation.

10 Claims, 1 Drawing Sheet

(56) References Cited

FOREIGN PATENT DOCUMENTS

| | | | | |
|---|---|---|---|---|
| CN | 102676592 | A | | 9/2012 |
| CN | 102965404 | A | * | 3/2013 |
| CN | 103060086 | A | | 4/2013 |
| CN | 108690838 | A | | 10/2018 |
| JP | S62287 | A | | 1/1987 |

OTHER PUBLICATIONS

International Search Report Dated Aug. 12, 2020, Application No. PCT/CN2020/085883.

* cited by examiner

METHOD FOR SYNTHESIZING DIGLYCERIDE

FIELD OF THE INVENTION

The present invention relates to a method for synthesizing a diglyceride.

BACKGROUND OF THE INVENTION

Diglyceride (Diacylglycerol, DAG) is a product for esterification of two hydroxyl groups on glycerol with fatty acids, a kind of natural component of oils and fats, and an intermediate product for metabolism of oils and fats. There are two kinds of DAG naturally present, which are divided into 1,2-DAG and 1,3-DAG, two isomers according to the difference of positions of hydroxyl groups at vacant sites. Since the diglyceride has a metabolism pathway different from that of triglyceride, DAG has functions of reducing blood lipid, alleviating diabetes and its complications, and inhibiting the accumulation of fats, and is a kind of healthy and safe functional oils and fats.

DAG can be prepared by a variety of processes, which mainly include a hydrolysis method, an esterification method, and a glycerolysis method. In the hydrolysis method, animal and vegetable oils and fats are subjected to a hydrolysis reaction by using a specific lipase for sn-1,3 positions, with refined animal and vegetable oils serving as raw materials, and DAG-rich samples are obtained by controlling the degree of hydrolysis. However, the degree of hydrolysis is difficult to be controlled, a large amount of by-product fatty acids may be produced, and the content of DAG is low. The glycerolysis for preparing diglyceride refers to using the lipase to catalyze a reaction of triglycerides and glycerol to obtain DAG. This method is subject to influences of a solvent, a type of an enzyme preparation, etc., and has a problem of low conversion rate.

The esterification method is currently a commonly used method for industrial preparation of diglyceride, which uses free fatty acids and glycerol as raw materials to synthesize diglyceride by catalysis of the lipase. Furthermore, DAG prepared by using a partial glycerol lipase may reach a purity of 90% or more after separation and purification. The products include diglycerides (DAG), monoglycerides (monoacylglycerol, MAG) and fatty acids (FFA). However, the method of using the partial glyceride lipase to catalyze esterification reaction to prepare diglyceride has a lower efficiency, and generally requires a longer reaction time, which seriously restricts industrial application prospects. Monoglyceride lipases generally have a stronger hydrolysis activity. Patent CN102965404A discloses a method for preparing a high-purity diglyceride. Wherein, the glycerol is subjected to an esterification reaction with a fatty acid, monoglyceride in the esterified product is hydrolyzed using a monoglyceride lipase, and the content of DAG reaches 98% after separation and purification by means of molecular distillation. However, the monoglyceride lipase generally has a weak esterification activity, and especially has a extremely low esterification activity to long-chain fatty acids. At present, there is no report that monoglyceride lipase can be used to catalyze the esterification of long-chain fatty acids to prepare glycerides.

SUMMARY OF THE INVENTION

An objective of the present invention is to provide a method for rapidly and efficiently synthesizing a diglyceride in order to address deficiencies present in the prior art. According to the method, a certain amount of monoglyceride lipase is added into a reaction system of preparing diglycerides by using partial glyceride lipase to catalyze long-chain fatty acids, and it is found that a catalytic efficiency of the partial glyceride lipase can be improved while without changing an equilibrium point of an esterification reaction, thereby significantly reducing time required for the esterification reaction to reach equilibrium.

The objective of the present invention is achieved by the following technical solutions:

A method for synthesizing a diglyceride, including: mixing a fatty acid donor with a glycerol, a partial glyceride lipase, and a monoglyceride lipase by adding water, subjecting the mixture to an esterification reaction, and performing further separation and purification to obtain the diglyceride.

Preferably, the partial glyceride lipase is one or a mixture of two of partial glyceride lipases, Lipase SMG1 derived from *Malassezia* and Lipase $G_{50}$, and the monoglyceride lipase is Lipase GMGL derived from marine *Geobacillus* sp.

Preferably, the partial glyceride lipase is added in an amount of 120 to 240 U/g based on a total mass of a reaction mixture; and the monoglyceride lipase is added in an amount of 60 to 240 U/g based on the total mass of the reaction mixture.

Preferably, a molar ratio of the fatty acid donor to the glycerol is 1:(0.3 to 10); and a mass ratio of the glycerol to the water is (10 to 30):1.

Preferably, the molar ratio of the fatty acid donor to the glycerol is 1:(3 to 4); and the mass ratio of the glycerol to the water is (14.2 to 28.4):1.

Preferably, the fatty acid donor is one or a mixture of two or more of a fatty acid, a low-carbon alkyl ester of fatty acid, or a raw material containing the fatty acid or the low-carbon alkyl ester of fatty acid.

Preferably, the fatty acid is one or a mixture of two or more of fatty acids having 6 to 22 carbon atoms.

The low-carbon alkyl ester of fatty acid is one or a mixture of two of methyl ester, ethyl ester, propyl ester, butyl ester, and pentyl ester.

Preferably, a time for the esterification reaction is 8 to 24 hours, more preferably, the time for esterification reaction is 12±2 hours.

Preferably, a temperature of the esterification reaction is 10 to 60° C. and a pH is 4 to 10.

Preferably, the temperature of the esterification reaction is 20 to 50° C. and the pH is 6 to 8.

Preferably, the temperature of the esterification reaction is 30 to 40° C.

Compared with the prior art, the present invention has the following advantages:

the present invention relates to the synthesis of the diglyceride by an enzymatic reaction using the partial glyceride lipase and the monoglyceride lipase together. When the partial glyceride lipase and the monoglyceride lipase are used together, a synthesis rate of the diglyceride is much higher than that when either of the partial glyceride lipase and the monoglyceride lipase is used alone, a synthesis time is shortened by half or more, and 45.50% or more of diglyceride is obtained after the esterification reaction. Since no triglyceride is generated in the product, the content of DAG is as high as 98% or more after purification by means of molecular distillation.

DETAILED DESCRIPTION OF THE EMBODIMENTS

Example 1

Figure 1:
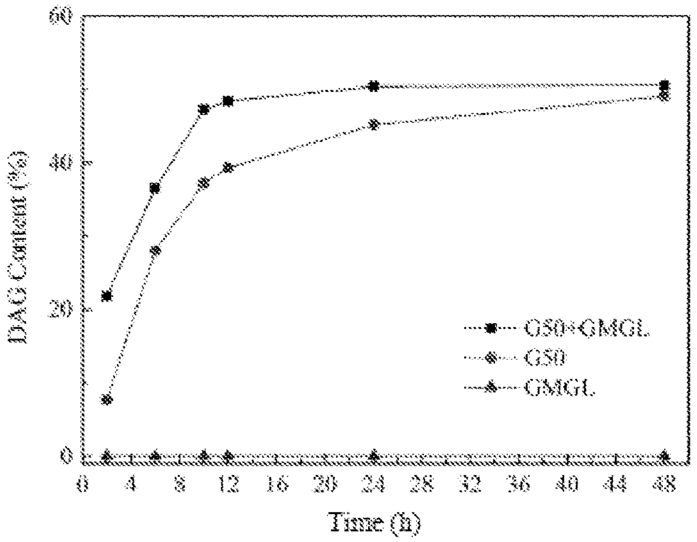
FIG. 1 is a graph of effects of Lipase $G_{50}$ and Lipase GMGL on the content of catalytically synthesized DAG in Example 1.
Figure 2:
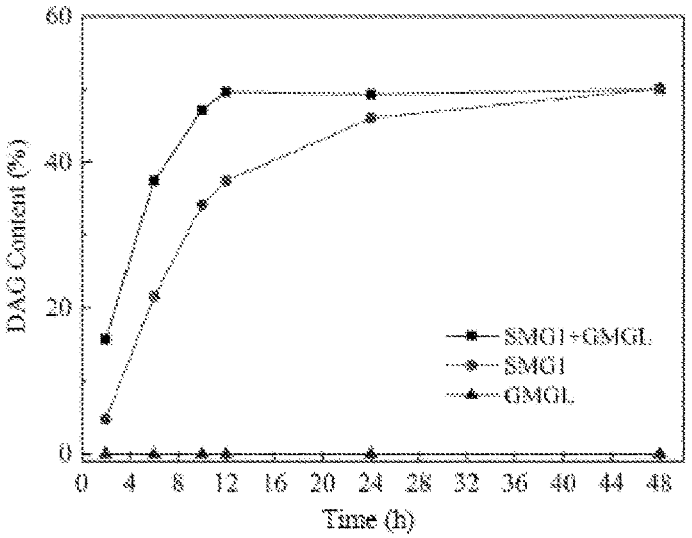
FIG. 2 is a graph of effects of Lipase SMG1 and Lipase GMGL on the content of catalytically synthesized DAG in Example 2.

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants, commercially available from Amano Enzyme Inc., Japan) was added and 240 U/g of monoglyceride lipase GMGL was added at the same time; and the mixture was subjected to reaction at a reaction temperature controlled to 35° C. for 12 hours. The content of DAG in an esterification product was 49.50%, and the content of DAG was as high as 98.07% after further separation and purification by means of molecular distillation.

Example 2

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added and 240 U/g of monoglyceride lipase GMGL was added at the same time; and the mixture was subjected to reaction at a reaction temperature controlled to 35° C. for 12 hours. The content of DAG in an esterification product was 50.04%, and the content of DAG was as high as 98.30% after further separation and purification by means of molecular distillation.

Example 3

4.3210 g of fatty acid, 5.6790 g of glycerol (a molar ratio being 1:4), and 0.2 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added and 240 U/g of monoglyceride lipase GMGL was added at the same time; and the mixture was subjected to reaction at a reaction temperature controlled to 35° C. for 12 hours. The content of DAG in an esterification product was 45.50%, and the esterification product was further separated and purified by means of molecular distillation.

Example 4

4.3210 g of fatty acid, 5.6790 g of glycerol (a molar ratio being 1:4), and 0.2 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added and 240 U/g of monoglyceride lipase GMGL was added at the same time; and the mixture was subjected to reaction at a reaction temperature controlled to 35° C. for 12 hours. The content of DAG in an esterification product was 46.01%, and the esterification product was further separated and purified by means of molecular distillation.

Example 5

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added and 60 U/g of monoglyceride lipase GMGL was added at the same time; and the mixture was subjected to reaction at a reaction temperature controlled to 35° C. for 12 hours. The content of DAG in an esterification product was 48.11%, and the esterification product was further separated and purified by means of molecular distillation.

Example 6

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added and 60 U/g of monoglyceride lipase GMGL was added at the same time; and the mixture was subjected to reaction at a reaction temperature controlled to 35° C. for 12 hours. The content of DAG in an esterification product was 49.01%, and the esterification product was further separated and purified by means of molecular distillation.

Example 7

5.0360 g of fatty acid, 4.9640 g of glycerol (a molar ratio being 1:3), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added and 240 U/g of monoglyceride lipase GMGL was added at the same time; and the mixture was subjected to reaction at a reaction temperature controlled to 35° C. for 12 hours. The content of DAG in an esterification product was 46.91%, and the esterification product was further separated and purified by means of molecular distillation.

Example 8

5.0360 g of fatty acid, 4.9640 g of glycerol (a molar ratio being 1:3), and 0.4 g phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added and 240 U/g of monoglyceride lipase GMGL was added at the same time; and the mixture was subjected to reaction at a reaction temperature controlled to 35° C. for 12 hours. The content of DAG in an esterification product was 46.10%, and the esterification product was further separated and purified by means of molecular distillation.

Comparative Example 1

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added; and the mixture was subjected to reaction at a reaction temperature controlled to 35° C. for 12 hours. The content of DAG in an esterification product was 39.30%, and the esterification product was further separated and purified by means of molecular distillation.

Comparative Example 2

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase GMGL (based on a total mass of reactants) was added, and the mixture was subjected to reaction at a reaction temperature controlled to 35° C. for 12 hours, and no DAG was substantially synthesized.

Comparative Example 3

4.3210 g of fatty acid, 5.6790 g of glycerol (a molar ratio being 1:4), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added; and the mixture was subjected to reaction at a reaction temperature controlled to 35° C. for 12 hours. The content of DAG in an esterification product was 37.42%, and the esterification product was further separated and purified by means of molecular distillation.

Comparative Example 4

4.3210 g of fatty acid, 5.6790 g of glycerol (a molar ratio being 1:4), and 0.2 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added; and the mixture was subjected to reaction at a reaction temperature controlled to 35° C. for 12 hours. The content of DAG in an esterification product was 35.20%, and the esterification product was further separated and purified by means of molecular distillation.

Comparative Example 5

4.3210 g of fatty acid, 5.6790 g of glycerol (a molar ratio being 1:4), and 0.2 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added; and the mixture was subjected to reaction at a reaction temperature controlled to 35° C. for 12 hours. The content of DAG in an esterification product was 35.02%, and the esterification product was further separated and purified by means of molecular distillation.

Comparative Example 6

5.0360 g of fatty acid, 4.9640 g of glycerol (a molar ratio being 1:3), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase Lipase $G_{50}$ (based on a total mass of reactants) was added; and the mixture was subjected to reaction at a reaction temperature controlled to 35° C. for 12 hours. The content of DAG in an esterification product was 36.30%, and the esterification product was further separated and purified by means of molecular distillation.

Comparative Example 7

5.0360 g of fatty acid, 4.9640 g of glycerol (a molar ratio being 1:3), and 0.4 g of phosphoric acid buffer solution with a pH of 7.5 were taken, added into a conical flask with a stopper, and mixed uniformly, and the conical flask was placed on a thermostatic magnetic stirrer with a rotation speed of 500 rpm for preheating at 35° C. for 10 minutes; after preheating was ended, 240 U/g of partial glyceride lipase SMG1 (based on a total mass of reactants) was added; and the mixture was subjected to reaction at a reaction temperature controlled to 35° C. for 12 hours. The content of DAG in an esterification product was 35.42%, and the esterification product was further separated and purified by means of molecular distillation.

The invention claimed is:

1. A method for synthesizing a diglyceride, comprising mixing one or more fatty acid donors with a glycerol, one or more partial glyceride lipases, a monoglyceride lipase, and water; subjecting the mixture to an esterification reaction; and separating and purifying to obtain the diglyceride;

the one or more partial glyceride lipases are one or a mixture of partial glyceride lipases, Lipase SMG1 derived from *Malassezia*, and Lipase $G_{50}$;

the monoglyceride lipase is Lipase GMGL derived from marine *Geobacillus* sp.; and a mass ratio of the glycerol to the water is (10 to 30):1.

2. The method according to claim 1, characterized in that the one or mixture of two partial glyceride lipases is added in an amount of 120 to 240 U/g based on a total mass of a reaction mixture; the monoglyceride lipase is added in an amount of 60 to 240 U/g based on the total mass of the reaction mixture.

3. The method according to claim 1, characterized in that a molar ratio of the fatty acid donor to the glycerol is 1:(0.3 to 10).

4. The method according to claim 3, characterized in that the molar ratio of the fatty acid donor to the glycerol is 1:(3 to 4); and the mass ratio of the glycerol to the water is (14.2 to 28.4):1.

5. The method according to claim 3, characterized in that the fatty acid donor is one or a mixture of two or more of a fatty acid, a low-carbon alkyl ester of fatty acid, or a raw material containing the fatty acid or the low-carbon alkyl ester of fatty acid; wherein the low-carbon alkyl is an alkyl having 1 to 5 carbon atoms.

6. The method according to claim 5, characterized in that, the one or more fatty acid donors are one or a mixture of two or more fatty acid donors having 6 to 22 carbon atoms; and the low-carbon alkyl ester of fatty acid is one or a mixture of two of methyl ester, ethyl ester, propyl ester, butyl ester, and pentyl ester.

7. The method according to claim 3, characterized in that a temperature of the esterification reaction is 10 to 60° C., a time for the esterification reaction is 8 to 24 hours, and a pH is 4 to 10.

8. The method according to claim 7, characterized in that the temperature of the esterification reaction is 20 to 50° C., the time for the esterification reaction is 12±2 hours, and the pH is 6 to 8.

9. The method according to claim 8, characterized in that the temperature of the esterification reaction is 30 to 40° C.

10. The method according to claim 2, characterized in that a molar ratio of the fatty acid donor to the glycerol is 1:(0.3 to 10); and a mass ratio of the glycerol to the water is (10 to 30):1.

* * * * *